United States Patent [19]

Koga et al.

[11] Patent Number: 4,732,906
[45] Date of Patent: Mar. 22, 1988

[54] DIOXOLOBENZIZOXAZOLE DERIVATIVES

[75] Inventors: Hiroshi Koga, Saitama; Takashi Dan, Tokyo; Haruhiko Sato, Tokyo; Etsuro Onuma, Tokyo, all of Japan

[73] Assignee: Chugai Seiyaki Kabushiki Kaisha, Tokyo, Japan

[21] Appl. No.: 840,680

[22] Filed: Mar. 18, 1986

[30] Foreign Application Priority Data

Apr. 8, 1985 [JP] Japan .................................. 60-74709
Jul. 18, 1985 [JP] Japan ................................. 60-159703

[51] Int. Cl.⁴ .......................................... C07D 261/20
[52] U.S. Cl. ...................................... 514/379; 548/242
[58] Field of Search ........................ 548/242, 207, 241; 549/434; 514/379

[56] References Cited

U.S. PATENT DOCUMENTS

| | | | |
|---|---|---|---|
| 3,758,506 | 1/1973 | Godfroid et al. | 549/478 |
| 4,217,349 | 8/1980 | Katsube et al. | 548/242 |
| 4,427,666 | 1/1984 | Mues et al. | 549/434 |
| 4,456,612 | 6/1984 | Plattner et al. | 548/242 |
| 4,560,558 | 12/1985 | Parks et al. | 548/241 |

OTHER PUBLICATIONS

Shutske et al, "[(3-Aryl-1,2-benzisoxasol-6-yl)oxy]acetic Acids, A New Diuretic Series", *J. Med. Chem.* vol. 25, 1982, pp. 36–44.

Plattner et al, "Substituted 5,6-Dihydrofuro[3,2-f]-1,2-benzisoxazole-6-carboxylic Acids; High-Ceiling Diuretics with Uricosuric Activity", *J. Med. Chem.*, vol 27, 1984, pp. 1016–1026.

*Primary Examiner*—Donald G. Daus
*Assistant Examiner*—B. Cassatt
*Attorney, Agent, or Firm*—Browdy and Neimark

[57] ABSTRACT

Dioxolobenzisoxazole derivatives of the formula

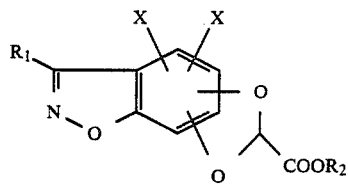

wherein $R_1$ is a phenyl group which may be substituted with a halogen atom, a lower alkyl group having 1–3 carbon atoms or a lower haloalkyl group, or a thienyl group; $R_2$ is a hydrogen atom or a lower alkyl group having 1–4 carbon atoms; and X and Y which may be the same or different represent a hydrogen atom or a halogen atom, as well as non-toxic salts thereof wherein $R_2$ is a hydrogen atom, a process for preparing the same and a pharmaceutical composition containing the same are disclosed.

The derivatives have diuretic and uricosuric activities and, therefore, are useful as a drug for treating hyperuricemia or hypertension.

6 Claims, No Drawings

DIOXOLOBENZIZOXAZOLE DERIVATIVES

This invention relates to dioxolobenzisoxazole derivatives having uricosuric and diuretic activities and represented by the formula (I):

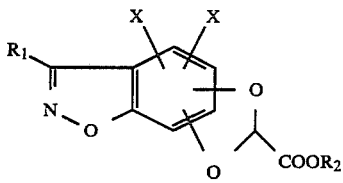

wherein $R_1$ is a phenyl group which may be substituted with a halogen atom, a lower alkyl group having 1-3 carbon atoms or a lower haloalkyl group, or a thienyl group; $R_2$ is a hydrogen atom or a lower alkyl group having 1-4 carbon atoms; and X and Y which may be the same or different represent a hydrogen atom or a halogen atom, and non-toxic salts thereof when $R_2$ is a hydrogen atom.

Conventional diuretic hypotensive agents are extensively used as drugs of first choice in the treatment of hypertension, but they have a high potential of causing hyperuricemia as a side effect. Furthermore, hypertension is often complicated by hyperuricemia and many cases of hyperuricemia are believed to be caused by disorders in the excretion of uric acid. Under these circumstances, there exists a strong need in medical fields for the development of diuretics having uricosuric activity.

Diuretics known to have uricosuric activity are phenoxyacetic acids typified by thienylic acid (U.S. Pat. No. 3,758,506), but the compounds are yet to be commercialized because of the high possibility of them causing liver disorders as a side effect.

As a result of various studies made to overcome these disadvantages, the present inventors have found that the dioxolobenzisoxazole derivatives of formula (I) have both uricosuric and diuretic activities and yet cause minimum side effects on the liver. The present invention has been accomplished on the basis of this finding.

In the compounds represented by the formula (I), the halogen atom of the halogen-substituted phenyl group for $R_1$ is chlorine, bromine, or fluorine. The lower alkyl-substituted phenyl for $R_1$ includes those substituted with an alkyl having 1-3 carbon atoms, preferably a tolyl group. An example of the haloalkyl-substituted phenyl is trifluoromethylphenyl.

On the other hand, the halogen atom for X and Y is chlorine, bromine or fluorine.

When $R_2$ is a hydrogen atom, the compounds of this invention may form salts with bases. Such salts should be pharmaceutically acceptable, and specific examples thereof are sodium salts, potassium salts, calcium salts, magnesium salts, ammonium salts, lower alkyl amine salts and ethanolamine salts.

The compounds of the formula (I) in accordance with the present invention are novel and specific examples thereof are
1,3-dioxolo[4,5-g]-1,2-benzisoxazole derivatives, and
1,3-dioxolo[4,5-f]-1,2-benzisoxazole derivatives.

The compounds of the formula (I) may be prepared by reacting a compound of the formula (II)

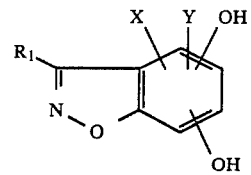

wherein $R_1$, X and Y are the same as defined above with a compound of the formula: $(A)_2CH-COOB$ wherein A is a halogen atom and B is a hydrogen atom or a lower alkyl group. The reaction is preferably performed in the presence of a base in an inert solvent. Examples of the inert solvent include ethers, alcohols, hydrocarbons, aromatic hydrocarbons, water, and aprotic polar solvents such as N,N-dimethylformamide and dimethyl sulfoxide. Illustrative bases are hydrides, alkoxides, hydroxides and carbonates of alkali metals and organic bases. More specific examples include sodium hydride, sodium methoxide, sodium ethoxide, sodium hydroxide, potassium hydroxide, sodium carbonate, potassium carbonate and triethylamine. The reaction temperature is appropriately selected from the range of 0° C. to about 150° C.

The isolation of the compounds of the formula (I) from the reaction mixture can be performed by conventional methods, for example, extraction, recrystallization, etc.

The compounds represented by the formula (II) may be prepared by subjecting the corresponding O-alkyl compounds to dealkylation reaction with pyridine hydrochloride, boron tribromide, etc.

The compound of this invention can be formulated with a pharmaceutically acceptable carrier by any conventional method into a preparation suitable for oral or parenteral administration.

The present invention will be further illustrated by the following Experiment and Examples, but they are not to be construed as limiting the invention.

PHARMACOLOGICAL ACTIVITIES OF THE COMPOUNDS

Experiment

The diuretic and uricosuric activities of the compounds of the present invention were confirmed by the following experiment.

Method:

Seven-week old Wistar-Imamichi rats that had been starved for 24 hours were divided into groups of four or five heads so that the animals of each group would excrete almost the same amount of urine. After forced urination, the rats were orally administered the test compounds that were suspended in physiological saline containing 3% gum arabic in a dose volume of 25 ml per kg of the body weight. The suspensions were administered typically in an amount of 100 mg/kg. Control rats were given only physiological saline containing 3% gum arabic. The animals were housed in separate metabolic cages and the urine excreted from each animal was collected over periods of 6 hours and 24 hours following the administration of the test compounds or physiological saline after complete starvation. The urine volume was directly read on a measuring cylinder after forced urination thereinto, and the amount of urine per kg of the body weight was calculated. The amount of uric acid excreted in the urine was determined by the uricase-catalase method.

Results:

As is apparent from the following Table I, the compounds of the present invention exhibited significant levels of diuretic and uricosuric activities, which were found to be long-lasting and dose-dependent. The compound numbers given in the table are keyed to the specific Examples shown later in this specification.

TABLE I

| | Amount of urine | | | | Amount of uric acid | | | |
|---|---|---|---|---|---|---|---|---|
| | 0–6 hours | | 0–24 hours | | 0–6 hours | | 0–24 hours | |
| Test Compound | (ml/kg) | (%) | (ml/kg) | (%) | (mg/kg) | (%) | (mg/kg) | (%) |
| Control group | 18.4 ± 1.4 | 100 | 35.2 ± 1.7 | 100 | 2.97 ± 0.17 | 100 | 10.62 ± 0.51 | 100 |
| Compound 12 | 33.1 ± 1.7 | 180.5$^c$ | 45.9 ± 1.5 | 130.2$^c$ | 3.67 ± 0.14 | 123.6$^b$ | 12.95 ± 0.57 | 122.0$^b$ |
| Control group | 17.7 ± 0.9 | 100 | 34.5 ± 1.3 | 100 | 2.99 ± 0.14 | 100 | 10.58 ± 0.52 | 100 |
| Compound 16 | 27.8 ± 1.5 | 156.8$^c$ | 42.3 ± 1.7 | 122.6$^b$ | 3.48 ± 0.19 | 116.3$^b$ | 11.90 ± 0.58 | 112.5 |
| Control group | 18.2 ± 1.6 | 100 | 35.1 ± 1.8 | 100 | 2.89 ± 0.16 | 100 | 10.26 ± 0.64 | 100 |
| Compound 17 | 62.6 ± 2.0 | 343.2$^c$ | 85.0 ± 5.1 | 242.4$^c$ | 3.80 ± 0.29 | 131.5$^a$ | 14.35 ± 0.96 | 139.9$^b$ |

$^a$ $p < 0.05$
$^b$ $p < 0.01$
$^c$ $p < 0.001$

EXAMPLE 1

A mixture of 5,6-dihydroxy-3-phenyl-1,2-benzisoxazole (2.9 g), potassium carbonate (10.7 g) and methyl dichloroacetate (3.7 g) in 50 ml of N,N-dimethylformamide was stirred at 90°–100° C. for 2.5 hours. After cooling, water (50 ml) was added to the mixture followed by stirring it at 90°–100° C. for 40 minutes. After cooling and acidifying the mixture with hydrochloric acid, the mixture was extracted with ether. The ether layer was washed with water, dried and evaporated to remove the solvent. The residue was washed with methylene chloride, recrystallized from acetone/water to give 2.0 g of 3-phenyl-1,3-dioxolo[4,5-f]-1,2-benzisoxazole-6-carboxylic acid. m.p.: 202.5°–203.5° C.

Analysis: Calcd. for $C_{15}H_9NO_5$: C, 63.61; H, 3.20; N, 4.95 (%). Found: C, 63.79; H, 3.26; N, 5.02 (%).

EXAMPLES 2–8

The compounds shown in Table II below were prepared by the method employed in Example 1.

TABLE 8

![structure showing R1, N-O, benzene ring with X and Y substituents, dioxolo ring with COOH]

| Example No. | Substituent | | | | Recrystallization medium |
|---|---|---|---|---|---|
| | R$^1$ | X | Y | m.p. (°C.) | |
| 2 | phenyl | H | Cl | 205.5–206.5 | acetonitrile/water |
| 3 | " | Cl | H | 246–247.5 | acetone/water |
| 4 | " | Cl | Cl | 231–232 | " |
| 5 | 2-thienyl | H | H | 214–218 (decomp.) | acetonitrile |
| 6 | 2-fluorophenyl | H | H | 245–248 (decomp.) | " |
| 7 | " | H | Cl | 212–214 (decomp.) | " |
| 8 | 2-chlorophenyl | H | H | 229–230 (decomp.) | " |

EXAMPLE 9

A mixture of 5,6-dihydroxy-3-(o-tolyl)-1,2-benzisoxazole (4.7 g), potassium carbonate (12.1 g), methyl dichloroacetate (4.2 g) in N,N-dimethylformamide (40 ml) was stirred at 90°–95° C. for 1.5 hours. After cooling, water (10 ml) was added to the mixture followed by stirring at 80°–90° C. for 10 minutes. After cooling the mixture was extracted with ether, and then the ether layer was washed with water, dried and evaporated to remove the solvent. The residue was dissolved in a potassium bicarbonate aqueous solution, and then ethanol was added to the solution. The resulting precipitate was collected by filtration, washed with ethanol and dried in air to give 3.1 g of 3-(o-tolyl)-1,3-dioxolo[4,5-f]-1,2-benzisoxazole-6-carboxylic acid potassium salt. The resulting potassium salt was dissolved in a small amount of water, and after acidifying it with hydrochloric acid, was extracted with ether. The ether layer was washed with water, dried and evaporated to remove the solvent. The residue was recrystallized from acetonitrile to give 1.9 g of 3-(o-tolyl)-1,3-dioxolo[4,5-f]-1,2-benzisoxazole-6-carboxylic acid. m.p.: 166–170 (decomposition)

The mass spectrum of this compound exhibited a molecular ion peak at m/e 297.

EXAMPLE 10

A mixture of 4-chloro-3-phenyl-1,3-dioxolo[4,5-f]-1,2-benzisoxazole-6-carboxylic acid (0.4 g) obtained in Example 3, conc. sulfuric acid (0.2 g) and absolute ethanol (10 ml) was refluxed for one hour. After distilling ethanol off, water was added to the mixture followed by extraction with methylene chloride. The methylene chloride layer was washed with water, dried and evaporated to remove the solvent. The residue was recrystallized from acetone/water to give 0.4 g of 4-chloro-3-phenyl-1,3-dioxolo[4,5-f]-1,2--benzisoxazole-6-carboxylic acid ethtyl ester. m.p.: 101.5°–102.5° C.

Analysis: Calcd. for $C_{17}H_{12}ClNO_5$: C, 59.06; H, 3.50; N, 4.05 (%). Found: C, 58.93; H, 3.50; N, 3.97 (%).

EXAMPLE 11

To a mixture of 6,7-dihydroxy-3-phenyl-1,2-benzisoxazole (2.8 g), methyl dichloroacetate (3.5 g) and N,N-dimethyl-formamide (50 ml) was slowly added 60% sodium hydride (1.2 g) while stirring under cooling with ice. After stirring for 5 hours at 90°–100° C., ice-water was added to the mixture followed by extraction with ether. The ether layer was washed with water, dried and evaporated to remove the solvent.

The residue was purified by a column chromatography on silica gel with use of dichloromethane as a developing solution. The resulting product was recrystallized from methanol/water to give 1.3 g of 3-phenyl-1,3-dioxolo[4,5-g]-1,2-benzisoxazole-7-carboxylic acid methyl ester. m.p.: 78°–80° C.

The mass spectorum of this product exhibited a molecular ion peak at 297 m/e.

EXAMPLE 12

A mixture of 6,7-dihydroxy-3-phenyl-1,2-benzisoxazole (2.1 g), potassium carbonate (7.7 g), methyl dichloroacetate (2.7 g) and N,N-dimethylformamide (50 ml) was stirred at 90°-100° C. for 5 hours. After addition of water (100 ml), the mixture was stirred at 90°-100° C. for 30 minutes, and after acidifying it with hydrochloric acid, extracted with ether. The ether layer was washed with water, dried and evaporated to remove the solvent. The residue was recrystallized from acetonitrile to give 1.5 g of 3-phenyl-1,3-dioxolo[4,5-g]-1,2-benzisoxazole-7-carboxylic acid. m.p.: 187°-190° C.

The mass spectrum of this product exhibited a molecular ion peak at m/e 283.

EXAMPLES 13-23

By the method similar to that described in Example 12, the compounds shown in Table III below were prepared.

TABLE III

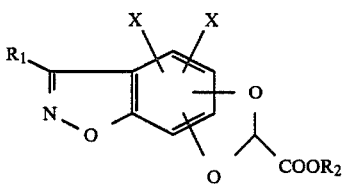

| Example No. | Substituent $R_1$ | X | Y | $R_2$ | m.p. (°C.) | Recrystallization medium |
|---|---|---|---|---|---|---|
| 13 | 2-fluorophenyl | H | H | H | 164–166 | dichloromethane |
| 14 | 2-chlorophenyl | H | H | K | 222–225 (decomp.) | water |
| 15 | 2-methylphenyl | H | H | K | 258–261 (decomp.) | water |
| 16 | phenyl | Cl | H | H | 149–150 | benzene |
| 17 | 4-fluorophenyl | H | H | H | 222–223 (decomp.) | acetonitrile |
| 18 | 2-thienyl | H | H | H | 226–228 (decomp.) | " |
| 19 | 4-chlorophenyl | H | H | H | 237–240 (decomp.) | " |
| 20 | 3-fluorophenyl | H | H | H | 191–193 | " |
| 21 | phenyl | H | Cl | H | 182–183 | " |
| 22 | 3-trifluoromethylphenyl | H | H | H | 194–197 (decomp.) | " |
| 23 | 4-fluorophenyl | H | Cl | H | 205–206 | acetone/water |

We claim:

1. A dioxolobenzisoxazole compound of the formula

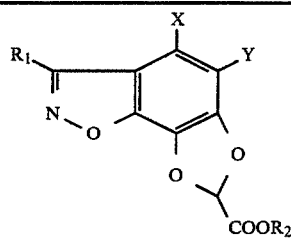

wherein $R_1$ is a phenyl group substitutable with a halogen atom, a lower alkyl group having 1-3 carbon atoms or a lower haloalkyl group, or a thienyl group; $R_2$ is a hydrogen atom or a lower alkyl group having 1-4 carbon atoms; and X and Y which may be the same or different represent a hydrogen atom or a halogen atom, and non-toxic salts thereof when $R_2$ is a hydrogen atom.

2. A compound according to claim 1 which is represented by the formula:

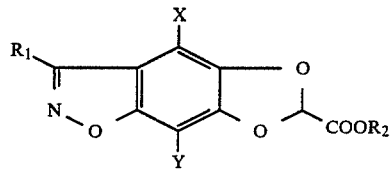

wherein $R_1$, $R_2$, X and Y are the same as defined above.

3. A compound according to claim 1 which is represented by the formula:

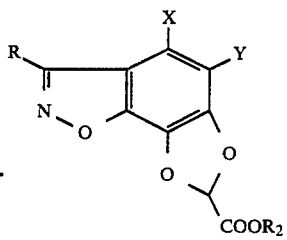

wherein $R_1$, $R_2$, X and Y are the same as defined above.

4. A pharmaceutical composition comprising a pharmaceutically acceptable carrier and a dioxolobenzisoxazole compound according to claim 1 in an amount effective to treat hyperuricemia or in an amount effective to treat hypertension.

5. A pharmaceutical composition according to claim 4 wherein said compound is present in an amount effective for treating hyperuricemia.

6. A pharmaceutical composition according to claim 4 wherein said compound is present in an amount effective for treating hypertension.

* * * * *